United States Patent [19]

Lunardi-Iskandar et al.

[11] Patent Number: 5,569,602
[45] Date of Patent: Oct. 29, 1996

[54] FIRST IMMORTALIZED KAPOSI'S SARCOMA CELL LINE

[75] Inventors: Yanto Lunardi-Iskandar, Gaithersburg; Robert C. Gallo, Bethesda, both of Md.

[73] Assignee: The United States of America as represented by the Secretary of the Department of Health and Human Services, Washington, D.C.

[21] Appl. No.: 110,175

[22] Filed: Aug. 20, 1993

[51] Int. Cl.$^6$ .................. C12N 5/00; C12N 5/08
[52] U.S. Cl. .................. 435/240.1; 435/240.2; 435/240.21
[58] Field of Search ............ 435/240.1, 240.20, 435/240.21

[56] References Cited

PUBLICATIONS

Ensoli et al., *Science* (1989) 243: 223–226.
Miles et al., *Science* (1992) 255: 1432–1434
Nair et al., *Science* (1992) 255: 1430–1432.
Nakamura et al., *Science* (1988) 242: 426–430.
Nakamura et al., *Science* (1992) 255: 1437–1440.
Northfelt, *Hematology/Oncology Clinics of North America* (1991) 5(2): 297–310.
Philip et al., *J. Acquired Immune Deficiency Syndromes* (1991) 4: 1254–1257.
Salahuddin et al., *Science* (1988) 242: 430–433.
Siegal et al., *Cancer* (1990) 65: 492–498.
Tsai et al., *US and Canadian Academy of Pathology Annual Meeting* (Mar. 5–10, 1989) p. 585 (Abstract).
Way et al., 1990, Clinical Research, 38(2):362A.
Way et al., 1990, Clinical Research, 38(1):133A.

*Primary Examiner*—Margaret Parr
*Assistant Examiner*—F. Christopher Eisenscheuk
*Attorney, Agent, or Firm*—Townsend and Townsend and Crew

[57] ABSTRACT

The present invention is related to immortalized cell lines. More particularly, the present invention is related to an immortalized Kaposi's sarcoma (KS) cell line derived from cells isolated from the pleural effusion of AIDS patients with KS. Monoclonal antibodies against KS cells are also provided, as are methods for evaluating antimalignancy therapies.

2 Claims, 3 Drawing Sheets

FIG. IA.
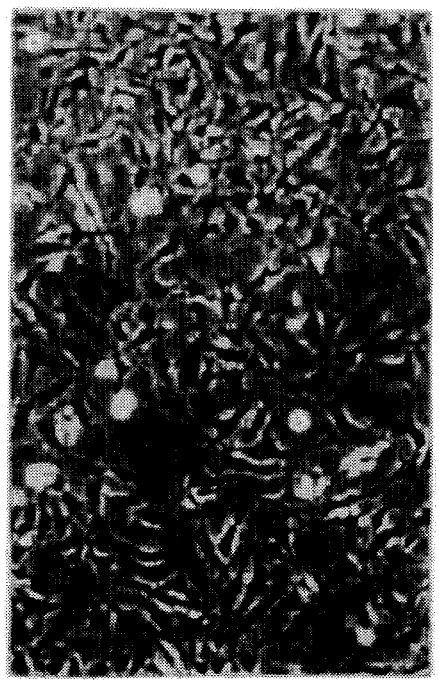
FIG. IB.

NUDE MICE

| 1 WEEK | 2 WEEKS | 3 MONTHS |

SCID MICE

| 1 WEEK | 2 WEEKS | 3 MONTHS |

NUDE MICE

| 1 WEEK | 2 WEEKS | 3 MONTHS |

SCID MICE

| 1 WEEK | 2 WEEKS | 3 MONTHS |

FIRST IMMORTALIZED KAPOSI'S SARCOMA CELL LINE

BACKGROUND OF THE INVENTION

Kaposi's sarcoma (KS) is the most common malignancy in patients with acquired immunodeficiency syndrome (AIDS) in the United States. Kaposi's Sarcoma is a multifocal neoplasm, consisting of several cell types and abundant angiogenesis. The tumor cell is believed to be a spindle-shaped cell and is usually considered to be of endothelial origin (Rutgers et al. (1986) *Am. J. Pathol.* 122: 493–499). However, its precise cellular origin and even its classification as a true monoclonal malignancy versus a polyclonal hyperplasia have remained elusive (Shaw et al. (1984) *Science* 226: 1165–1171; Holden et al. (1989) *J. Invest. Dermatol.* 93: 119S–124S; Hashimoto et al. (1987) *Pathol. Res. Pract.* 182: 658–668). The isolation of a Kaposi's sarcoma cell line would aid in elucidating the mechanism of KS induction and pathogenesis.

A major problem in treating Kaposi's sarcoma is that most or all of the known therapies have serious adverse effects, including myelotoxicity and neurotoxicity (see, e.g. Northfeldt et al. (1991) *Hematology/Oncology Clinics of North America* 5: 297–310, which is incorporated herein by reference). These therapies can also induce immunosuppression, compounding the pre-existing immunodeficiency that is usually present in AIDS patients. Thus, a great need exists for a system for testing anti-Kaposi's sarcoma therapies without having to subject human patients to the trial and error process of optimizing combinations and dosages of therapeutic agents or procedures.

The isolation of an immortal malignant Kaposi's sarcoma cell line would provide such a system. Such a cell line would provide a system for assaying antitumor drugs and other therapies that can be useful in reducing growth and metastatic spread of KS cells in vivo. A malignant KS cell line would also allow the development of novel antitumor therapies, such as the production of a KS-specific monoclonal antibody that is useful for diagnosis or for targeting therapeutic drugs. Studies of the hormonal, immunological, virological, and cytokine-mediated factors that influence the development and metastasis of malignancies would also be facilitated by the development of a malignant KS cell line.

No previously isolated KS cell line is capable of continuous growth absent growth factors and is also tumorigenic. Nakamura et al. ((1988) *Science* 242: 426–430, which is incorporated herein by reference) previously reported KS cell strains that required growth factors such as those contained in conditioned medium (CM) from retrovirus-infected CD4$^+$ T-lymphocytes for growth. These KS cell strains survived for at least 236 days when grown in conditioned medium, but for only 36 days when grown in the absence of conditioned medium. Subcutaneous injection of these KS cells into nude mice induced angiogenic lesions, however the lesions regressed after 6 days and no tumors formed. Cells from these lesions were all of mouse origin, as determined by chromosome analysis.

Tsai et al. isolated a Kaposi's sarcoma-like cell line from simian AIDS with retroperitoneal fibromatosis (RF), but this line does not induce tumor growth in mice (Tsai et al. *United States and Canadian Academy of Pathology Annual Meeting*, Mar. 5–10, 1989, p. 585).

Philip et al. isolated the KSC-8 cell strain from a Kaposi's sarcoma patient (Philip et al. (1991) *J. Acquired Immune Deficiency Syndromes*, 4: 1254–1257, which is incorporated herein by reference). KSC-8 cells have multiple large chromosomal rearrangements and are pseudoploid. This strain induced tumors after intraperitoneal injection into nude mice, but there is no indication of how long KSC-8 can survive in culture. Moreover, and unlike the cells of this invention, the KSC-8 cells lack *Ulex europaeus* agglutinin 1 (UEA-1) binding ability. Thus, the Kaposi's sarcoma phenotype of these cells cannot be conclusively established.

The cell line disclosed herein, in contrast to those cell strains previously reported, fulfills the needs discussed above, and others. The cell line provides a means for testing anti-Kaposi's sarcoma therapies in vitro, or in a model animal system, rather than in a human patient. This allows therapies to be tested and dosages to be optimized before testing the therapies in humans. The cell line also provides a means of developing novel antitumor therapies and also serves as a source of known and novel growth factors. Also, the cell line will facilitate studies of factors that influence the development and metastasis of malignancies.

SUMMARY OF INVENTION

The present invention provides immortal Kaposi's sarcoma (KS) cell lines. The cell lines produce long-lasting human tumors when injected into a host animal such as a mouse. The cell lines, which typically have a tetraploid karyotype and bind to UEA-1, do not require exogenous growth factors for growth in vitro. Methods for obtaining KS cell lines are also provided. The present invention also provides monoclonal antibodies that specifically recognize Kaposi's sarcoma, and methods for producing such antibodies. Also provided are methods for testing antitumor and antimetastasis therapies that involve culturing cells of a KS cell line, treating the cells with the antitumor or antimetastasis therapy, and determining whether growth of the cells is inhibited or injecting the cells into a host animal and determining whether a tumor is formed or metastasis occurs.

BRIEF DESCRIPTION OF THE FIGURES

FIGS. 1A–1D show the morphology and karyotype of KS Y-1 cells cultured in the absence or presence of 20% (volume) HTLV-II-infected T cell conditioned medium (CM). FIG. 1A) morphology of cells grown in absence of CM; FIG. 1B) morphology of cells grown in presence of CM; FIG. 1C) karyotype of KS Y-1 cells grown in absence of CM; FIG. 1D) karyotype of KS Y-1 cells grown in presence of CM. Translocated dicentric chromosomes are indicated by arrows; markers of unknown origin are marked as "M."

DESCRIPTION OF THE PREFERRED EMBODIMENT

Definitions

Figure 2A:
FIGS. 2A and 2B show tumorigenesis induced by KS Y-1 cell line when injected into nude and SCID mice ($5\times10^4$ to $5\times10^6$ cells (see FIG. 2A), and histological appearance of subcutaneous lesions induced by KS Y-1 cell line (see FIG. 2B).
Figure 2A:
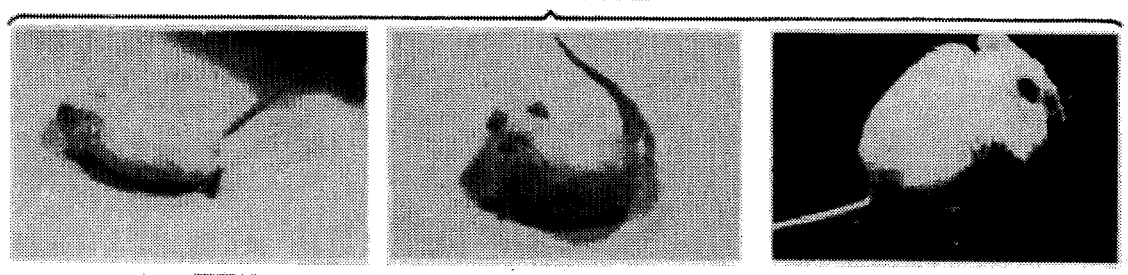

The term "cell line," as used herein, refers to individual cells, harvested cells, and cultures containing the cells, so long as they are derived from cells of the cell line referred to. A cell line is said to be "continuous," "immortal," or "stable" if the line remains viable over a prolonged time, typically at least about six months. To be considered a cell line, as used herein, the cells must remain viable for at least 50 passages in the absence of exogenous growth factors. A "cell strain," in contrast, refers to cells that do not remain viable over a prolonged time in the absence of exogenous growth factors.

A cell line is said to be "malignant" if, when the cell line is injected into a host animal, the host animal develops tumors or cancers that are anaplastic, invasive, and/or metastatic. A "human" tumor is comprised of cells that have human chromosomes. Such tumors include those in a human patient, and tumors resulting from the introduction of a human malignant cell line into a non-human host animal if cells from such tumors have human chromosomes. A tumor is said to be "long-lasting" when the tumor persists in an animal for at least about one month.

A cell is said to have a "tetraploid karyotype" if it contains four complete or substantially complete sets of chromosomes. A human tetraploid cell will have about 92 chromosomes, four times the normal haploid number.

"Growth factors" include one or more of Oncostatin M, tumor necrosis factor α, interleukin-1, interleukin-2, interleukin-2, and the HIV-1 transactivator TAT. Several growth factors have been identified in HTLV-II-conditioned medium (HTLV-II CM), obtained by growing HTLV-II-infected $CD4^+$ T lymphocytes. One of these factors, oncostatin-M (Zarling et al. (1986) *Proc. Natl. Acad. Sci. USA*, 83: 9739–9743; Nair et al. (1992) *Science* 255: 1430–1432), is a 30 kD growth regulator originally identified by its ability to inhibit the growth of A375 melanoma cells and other human tumor cell lines, and to stimulate the proliferation of normal human fibroblasts and endothelial cells (Miles et al. (1992) *Science* 255: 1432–1434; Brown, T. J. (1987) *J. Immunol.* 139: 2977–2983).

The growth of a cell line is said to be "inhibited" if, when assayed by means such as radioisotope incorporation into the cells, the treated cells proliferate at a rate that is less than about 80% of the proliferation rate of untreated control cells, and preferably less than about 70% of the untreated cell proliferation rate.

"Monoclonal antibody" refers to an antibody produced by a clonal, immortalized cell line separate from cells producing antibodies with a different antigen binding specificity. Thus, such monoclonal antibodies are produced isolated from other monoclonal antibodies and, accordingly, in substantially pure form (relative to other antibodies) and at a concentration generally greater than normally occurring in sera from the animal species which serves as a B cell source.

Monoclonal antibodies can be obtained by various techniques familiar to those skilled in the art. Briefly, spleen cells from an animal immunized with a desired antigen are immortalized, commonly by fusion with a myeloma cell (see, Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells can be enhanced by various techniques, including injection into the peritoneal cavity of a vertebrate host. As used herein, the term "monoclonal antibody" also refers to fragments of such antibodies that retain the ability to bind to the particular antigen.

An antibody "specifically recognizes" or "selectively recognizes" an antigen if the antibody binds to a cell or other carrier that carries the antigen and does not bind to a cell or carrier that does not carry the antigen.

DETAILED DESCRIPTION

Novel immortal malignant cell lines derived from a Kaposi's sarcoma, methods of preparing these cell lines, and methods of using these cell lines are included in the present invention. One such cell line, KS Y-1, was deposited under the Budapest Treaty with the American Type Culture Collection (12301 Parklawn Drive, Rockville Md. 20852) on Aug. 20, 1993, and has been assigned ATCC Accession No. CRL 11448.

Preparing Malignant KS Cell Lines

The cell lines of the present invention can be derived from cells obtained from an acquired immunodeficiency syndrome (AIDS) patient having Kaposi's sarcoma. For example, cells can be separated from pleural effusion material (see, e.g., Batungwanayo, J. et al. (1993) *AIDS* 7: 73–79) obtained from a patient by using FICOLL-PAQUE (Pharmacia LKB Biotechnology, Piscataway, N.J., used as directed by the manufacturer). The cells are then pelleted by low speed centrifugation for 30 min. at 1300 rpm. Alternatively, KS cells can be obtained from solid tumors obtained, for example, from lung biopsies and other lesions from Kaposi's sarcoma patients. Briefly, the tumors are minced into fragments of approximately 1–2 mm diameter and treated with trypsin (0.25%) and EDTA. The tumor fragments are incubated in the enzyme solution at 37° C. for 30 hours. Then the solution is centrifuged for 15 min. at 1300 rpm, filtered, and treated again with the trypsin solution for 30 min. at 37° C. The solution is then centrifuged as above, and the pellet contains the tumor cells.

The cells thus obtained from the Kaposi's sarcoma patient are enriched for KS cells by selectively removing T lymphocytes, monocytes, macrophages, and fibroblasts by complement-mediated cytotoxicity (see, e.g., *Immunological Methods*, Lefkovits, I. and B. Pernis, Eds., Academic Press, New York, which is incorporated herein by reference) using monoclonal antibodies against cell surface antigens characteristic of each particular cell type (Becton Dickinson, Mountain View Calif.). For example, antibodies against the CD2, CD3, CD4, and CD8 antigens are used to eliminate T cells, antibody against CD10 eliminate fibroblasts, and anti-CD14 antibody eliminates macrophages and monocytes. Briefly, the cells (about $10^6$) are suspended in medium (such as RPMI1640 (see, e.g., Gibco/BRL Catalogue & Reference Guide, Gaithersburg, Md., 1992, p. 105) +10% fetal calf serum (FCS) (RPMI-FCS)) containing 10 μg of each antibody and incubated at 4° C. for 30 min. Nontoxic rabbit complement (Cedarlane Hornby, Ontario, Canada), diluted 1:38 in RPMI-FCS, is then added and the cells are incubated for 40 min. at 37° C. If desired, the dead cells can be removed after fixation by layering the cell suspension over a cushion of FICOLL-PAQUE (Pharmacia, Piscataway, N.J.) and centrifuging for 15 min. at 1400 rpm at room temperature. Viable cells are recovered from the FICOLL-medium interface and washed twice in cold RPMI-FCS.

To select for malignant cells, the resulting KS cell-enriched population is grown in the absence of any exogenous growth factors. Suitable media for growing and maintaining the malignant cells obtained include, for example, RPMI1640+10% fetal calf serum (Gibco/BRL, Gaithersburg Md.), supplemented with 1% Nutridoma (Boehringer Mannheim, Indianapolis Ind.), 1% glutamine (Gibco/BRL), 1% amino acid solution (Gibco/BRL), non-essential amino acid solution (Gibco/BRL), and antibiotics (penicillin and streptomycin, Gibco/BRL). Other media suitable for growth of mammalian cells can also be used (see, e.g. Gibco/BRL 1992 Catalog).

Cells that grow in the absence of exogenous growth factors are then analyzed to determine whether they are indeed a malignant Kaposi's sarcoma cell line. The cells are tested to determine whether they are capable of inducing tumors in nude or SCID mice. For example, nude mice (Beige, BALB/c, Swiss, or NCr (see, e.g., Croyba et al. (1993) *Laboratory Animal Science*, 43: 120–122)) are inoculated subcutaneously with $4 \times 10^6$ cells. The cells of the present invention will typically induce a strong angiogenic reaction at the site of inoculation within seven days. Tumors will usually develop and persist for at least three months. These tumors can occur at the site of injection and also as metastases in one or more of the lung, spleen, skin, or pancreas. Typically, tumors induced by the KS cell lines of the present invention will metastasize.

A karyotype analysis is performed according to methods known to those skilled in the art, usually by microscopic examination of cells at metaphase. See, e.g., *Cytogenet. Cell Genet.* (1981) 31: 11–18; McKusick et al. (1993) *J. Med. Genet.* 13: 1–26; Solomon et al. (1991) *Science* 254: 1153–1160) The cell lines of the present invention will typically have a chromosome number that is in the tetraploid range. Multiple marker chromosomes and translocated dicentric chromosomes are commonly observed in these cell lines. Cells from tumors induced by the cell lines disclosed herein typically will also contain human chromosomes, as determined by karyotype analysis.

To further confirm the Kaposi's sarcoma phenotype of the cells, tests are performed to detect the presence or absence of markers that are characteristic of KS cells. For example, the ability of the cells to bind *Ulex europaeus* agglutinin 1 (UEA-1) is tested. UEA-1 is a lectin that binds to α-L-fucose residues on cell membranes, and is found on Kaposi's sarcoma cells (Orodenez and Batskis (1984) *Arch. Pathol. Lab. Med.* 108: 129–132; Beckstead et al. (1985) *Am. J. Pathol.* 119: 294–300; Russell-Jones et al. (1986) *J. Clin. Pathol.* 39: 742–749; Miettinen et al. (1983) *Am. J. Clin. Pathol.* 79: 32–36). In brief, cells are incubated with UEA-1 (0.002% UEA-1 (Dako Corp., Carpenteria Calif.) in 0.5% bovine serum albumin (Sigma Chemical Co.)), washed, incubated with rabbit anti-UEA-1 antibody (Dako Corp.), washed again, and incubated with, for example, a FITC-conjugated goat anti-rabbit immunoglobulin antibody (Sigma Chemical, St. Louis Mo.). After final washes, the cells are examined by phase contrast and fluorescence microscopy to detect UEA-1 binding. Cells of the present invention will bind UEA-1.

Similar tests can be performed using monoclonal antibodies against other markers that are characteristically present or absent in Kaposi's sarcoma cells. For example, factor VIII-related antigen, CD31, PAL-E and EN-4 (Holden, C. A. (1989) *J. Invest. Dermatol.* 93: 1195–1245; Jaffe et al. (1973) *J. Clin. Invest.* 52: 2757–2764; Burgdor et al. (1981) *Am. J. Clin. Pathol.* 75: 167–171; Cui et al. (1983) *Immunol.* 49: 183–189) are present on vascular endothelial cells, but usually not on the KS cell lines of the present invention. Fibronectin and ICAM-1, which are expressed by many mesenchymal cells (Jaffe et al., supra.) are also usually expressed by the cell lines disclosed herein. The cell lines also bind antibodies against smooth muscle α-actin (Amac Corp., Westbrook Me.).

Following the above procedures, KS cell lines can be obtained from most KS patients.

Characteristics of Kaposi's Sarcoma Malignant Cell Lines

The cell lines of the present invention have several properties that provide significant advantages over previously reported cell strains derived from Kaposi's sarcoma patients. The cell lines disclosed herein are capable of growing in continuous culture for an indefinite period (at least 90 passages) while maintaining the properties of Kaposi's sarcoma cells. These KS cells also generate long-lasting metastasizing tumors when injected into a host animal, such as a mouse. The tumors resulting from injection of the cell lines have human chromosomes, rather than the chromosomes of the host animal.

In addition, the cell lines of this invention will have at least three, and typically four, of the following five properties: a) typical chromosome number in the tetraploid range; b) contain multiple marker chromosomes and translocated dicentric chromosomes; c) lack ability to bind the PAL-E or EN-4 antibodies, or antibodies against factor VIII-related antigen; d) express CD31, fibronectin, ICAM-1, IL-6 receptor, IL-8 receptor, and vascular endothelial growth factor; and e) bind *Ulex europaeus* agglutinin 1 (UEA-1) and antibodies against smooth muscle α-actin. The human leukocyte antigen (HLA) type of the KS cell lines will be the same as that of the KS patient from which the cells were derived. HLA typing is described in, for example, Bodmer, W. F., *Histocompatibility Testing*, Ed. Albert, P. et al., Springer-Verlag KG, Berlin, 1984.

The cell line disclosed herein is capable of growing in continuous culture for an indefinite period while maintaining the properties of Kaposi's sarcoma cells. Exogenous growth factors are not required for in vitro growth of the KS cell lines of the present invention. In contrast, previously disclosed Kaposi's sarcoma cell strains do require growth factors for growth in culture (Nakamura et al., supra.). For example, these strains require growth factors produced by retrovirus-infected (HTLV-I, HTLV-II, HIV-1, and HIV-2) T lymphocytes, such as oncostatin M, for growth in vitro.

The KS cell lines of the present invention generate long-lasting tumors (persisting at least one month, and often for more than 3 months) after injection into nude and SCID mice. These tumors, which occur at the site of injection and also as metastases in the lung, spleen, skin, and pancreas, have a human karyotype and have similar chromosomal abnormalities to the cell line that induced the tumors. Initially after injection, angiogenic lesions are induced that are similar at day 7 to those induced by the KS cell strains reported by Salahuddin et al. (1988 *Science* 242: 430–433). However, the lesions induced by these previously reported strains do not form solid tumors and do not metastasize. The KSC-8 cell line (Philip et al., supra.), which is reported to induce tumors when injected into nude mice, does not have the Kaposi's sarcoma phenotype.

Tumors induced by the cells of the present invention are composed of cells that have human chromosomes. In contrast, the lesions induced by injecting the previously reported cell strains into a mouse have a normal mouse karyotype, and are probably mediated by cytokine release from the injected cell strains.

Similar to other tumor cells (Levenbook et al. (1985) *J. Biol. Stand.* 13: 135–141), the cell line of the present invention grows efficiently in methylcellulose (approximately 300 colonies formed from $10^4$ cells plated).

The KS cell lines of the present invention usually have a chromosome number that is in the tetraploid range. Numerous chromosomal abnormalities are typically present in these KS cells, such as multiple marker chromosomes and translocated dicentric chromosomes. These abnormalities are typically present in primary cells and after extensive passaging in vitro (more than 70 passages), whether the cells are cultured in the presence or absence of activated T-cell cultured medium.

The KS cell lines of the present invention are apparently mesenchymal and have properties of both vascular smooth muscle cells and endothelial cells, but also are different from these two cell types in some properties (Table 1). For example, vascular endothelial cells (such as human umbilical vein endothelial cells (HUVEC)) express factor VIII-related antigen and CD31, and bind the anti-cell surface antigen monoclonal antibodies PAL-E and EN-4. (Holden, C.A., supra.; Jaffe et al., supra.; Burgdor et al., supra.; Cui et al., supra.). In contrast, the KS cell lines disclosed herein typically do not have these markers. Human aortic smooth muscle cells (HASMC) and a previously disclosed non-malignant KS cell strain also lack these markers.

Fibronectin and ICAM-1 are expressed on the cell lines disclosed herein, as well as on KS-3 cells, H-UVEC, and HASMC. The abbreviation UEA-1, as used herein, refers to *Ulex europaeus* agglutinin 1. UEA-1 is a marker for endothelial cells, while fibronectin and ICAM-1 are expressed by many mesenchymal cells (Jaffe et al., supra.).

Uses of the KS Cell Lines

The cell lines of the present invention are useful in in vivo and in vitro assays to identify effective antitumor drugs and other therapies that are effective in reducing the growth potential and metastatic spread of KS cells in vivo. As used herein, an antitumor therapy includes those therapies that are known to be effective against tumors, and also therapies that are potentially effective. An antimetastasis therapy is a therapy that reduces or eliminates metastasis, or can potentially limit metastasis.

TABLE 1

Comparison of the phenotype of the KS Y-1 cell line to that of the KS-3 cell strain, human umbilical vein endothelial cells (HUVEC) and human aortic smooth muscle cell (HASMC).

| Smooth muscle | HUVEC | KS Y-1 | KS-3 | HASMC |
|---|---|---|---|---|
| PAL-E | + | − | − | −* |
| EN-4 | + | − | − | −* |
| ICAM-1 | ++ | ++ | ++ | ++ |
| Factor VIII | +++ | − | − | −* |
| CD31 | +++ | +++ | +++ | − |
| Fibronectin | + | ++ | ++ | ++ |
| Smooth muscle alpha actin | − | ++++ | ++ | ++++* |
| UEA-1 | +++ | +++ | +++ | |
| CD10 | − | − | − | |
| CD4 | − | − | − | − |
| CD14 | − | − | − | − |
| IL-2R p55 | +++ | +++ | ++ | ++ |
| IL-2Rp75 | ++ | ++ | ++ | ++ |
| CD71 | ++ | ++ | ++ | ++ |
| HC-R | ++ | ++ | ++ | ND |

Reactivities are shown as: −, negative; ++, positive: +++, moderately positive: ++++ strongly positive ND, Not done, *B. Ensoli et al., unpublished data.

Among the potential antitumor therapies that can be tested using the present invention is chemotherapy. Potential anti-Kaposi's sarcoma agents include zidovudine (AZT), vinblastine, vincristine, etoposide, idarubicin, mitoxantrone, doxorubicin, epirubicin, and others (see, Northfeldt et al., supra). The agents listed above have been used alone and in combination with each other, and with other agents such as bleomycin (Id.).

Other potential antitumor therapies that may prove useful for treating KS include interferon α and β, and tumor necrosis factor. Radiation therapy is very useful for treating KS, but patients are often unusually sensitive to radiation, resulting in severe mucositis. Liquid nitrogen treatment and laser phototherapy are also used for KS management (Id.).

The therapies discussed above often cause severe adverse reactions in human patients, and dosages must often be reduced, so the model system provided by the cell line disclosed herein is useful for optimizing these and other therapies to minimize adverse reactions and maximize the anti-KS activity.

A further use for the cell lines of the present invention is in the study of the underlying mechanisms of angiogenesis, tumorigenesis, and metastasis. The KS Y-1 cell line is capable of in vitro growth independent of exogenous growth factors, possesses an abnormal karyotype, and is capable of inducing malignant tumors in SCID and nude mice. These cell strains may represent an early stage of KS at which the lesions have a multifocal pathology and are polyclonal. The KS Y-1 cell line disclosed herein may represent a latter stage of Kaposi's sarcoma at which a true monoclonal tumor evolves. A systematic study of the differences between the KS cell strains and KS Y-1 will aid in elucidating the important steps between hyperplasia and neoplasia.

The cell lines disclosed herein are also useful for producing growth factors or cytokines, including possible novel compounds. Known growth factors produced by non-malignant KS cell strains include interleukin-1β, basic fibroblast growth factor, granulocyte-monocyte colony-stimulating factor, transforming growth factor β, and platelet-derived growth factor B (Ensoli et al. (1989) *Science* 243: 223–226). The immortal malignant KS cell lines of the present invention will be a more useful source of these and other growth factors than the previously reported KS cell strains because the cells disclosed herein can be grown indefinitely in the absence of exogenous growth factors.

Monoclonal Antibodies Specific for Kaposi's Sarcoma

The cell lines disclosed herein are also useful for producing a Kaposi's sarcoma-specific monoclonal antibody that is useful for diagnosing and treating Kaposi's sarcoma. Various techniques useful in these arts are discussed, for example, in Harlow and Lane, *Antibodies: A Laboratory Manual,* Cold Spring Harbor, New York (1988) (incorporated herein by reference for all purposes), including: immunization of animals to produce immunoglobulins; production of monoclonal antibodies; labeling immunoglobulins for use as probes; immunoaffinity purification; and immunoassays.

The anti-Kaposi's sarcoma monoclonal antibodies of the present invention can be prepared by immunizing an animal with cells of the malignant KS cell lines. The animals immunized can be any one of a variety of species which are capable of immunologically recognizing epitopes characteristic of these KS cells, such as mouse, rabbit, horse, etc. Spleen cells from these immunized animals are then immortalized by techniques known to those skilled in the art. Briefly, an animal is inoculated with an immortal malignant Kaposi's sarcoma cell line. B lymphocytes are isolated from the animal and fused with malignant mammalian B lymphocytes to produce hybridomas.

The hybridomas or lymphoblastoid cells that secrete antibodies of interest can be identified by screening culture supernatants for antibodies that specifically recognize the KS cell lines of the present invention, and do not specifically recognize non-malignant or non-KS cells. For example, the immortal malignant KS cells disclosed herein can be added to the wells of microculture plates, cultured until confluent, the monolayers washed, and a hybridoma culture supernate added to each well. In parallel experiments, the hybridoma culture supernates are also added to wells that contain monolayers of non-malignant KS cells, or non-KS cells. Bound antibodies are detected by methods known to those skilled in the art. Hybridoma cultures that produce antibodies that bind to the malignant KS cell lines are selected, recloned, and maintained.

Alternatively, a screening assay can be employed to detect those antibodies that are cytotoxic to the KS cell lines disclosed herein. Cells that possess the desired activity are cloned and subcloned in accordance with conventional techniques and monitored until stable, immortalized lines producing the anti-KS monoclonal antibody of interest are identified.

The anti-KS monoclonal antibodies of the invention, and fragments thereof, find utility in therapeutic and diagnostic methods and compositions. Genes encoding the antibodies of the invention, in whole or in part, can be combined with functional regions from other genes (e.g., enzymes), or with other molecules such as toxins or labels to produce fusion proteins (e.g., "immunotoxins") having novel properties. In these cases of gene fusion, the two components are present within the same polypeptide chain. Alternatively, the immunoglobulin or fragment thereof can be chemically bonded to the toxin or label by any of a variety of well-known chemical procedures. For example, when the label or cytotoxic agent is a protein and the second component is an intact immunoglobulin, the linkage can be by way of heterobifunctional cross-linkers, e.g., SPDP, carbodiimide, glutaraldehyde, or the like.

Therapeutic Uses

For therapeutic uses, anti-KS monoclonal antibodies are used as a cytotoxic agent against Kaposi's sarcoma cells in vivo, either in conjunction with complement or by attaching a toxic molecule to the antibody. Production of various immunotoxins is well-known with the art, and methods can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982); E. Vitetta, *Science* (1987) 238:1098–1104; and G. Winter and C. Milstein, Nature (1991) 349:293–299; all incorporated herein by reference.

A variety of cytotoxic agents are suitable for use in immunotoxins, such as radionuclides, such as Iodine-131, Yttrium-90, Rhenium-188, and Bismuth-212; a number of chemotherapeutic drugs, such as vindesine, methotrexate, adriamycin, and cisplatinum; and cytotoxic proteins such as ribosomal inhibiting proteins (pokeweed antiviral protein, Pseudomonas exotoxin A, ricin, diphtheria toxin, ricin A chain, etc.), or an agent active at the cell surface, such as the phospholipase enzymes (e.g., phospholipase C). (See, generally, "Chimeric Toxins," Olsnes and Pihl, *Pharmac. Ther.*, 15:355–381 (1981), and "Monoclonal Antibodies for Cancer Detection and Therapy," eds. Baldwin and Byers, pp. 159–179, 224–266, Academic Press (1985), both of which are incorporated herein by reference).

For pharmaceutical compositions, the anti-KS monoclonal antibodies of the invention, or fragments thereof, as described herein are administered to an individual having Kaposi's sarcoma. In therapeutic applications, compositions are administered to a patient in an amount sufficient to cure or at least partially arrest the tumorigenesis and its symptoms and/or complications. An amount adequate to accomplish this is defined as "therapeutically effective dose." Amounts effective for this use will depend on, e.g., the nature of the anti-KS monoclonal antibody, the manner of administration, the stage and severity of the Kaposi's sarcoma, the weight and general state of health of the patient, and the judgment of the prescribing physician, but will generally range from about 0.01 mg/kg to about 100.0 mg/kg of antibody per day, with dosages of from about 0.1 mg/kg to about 10.0 mg/kg of antibody per day being more commonly used. Humanized versions of anti-KS monoclonal antibodies of the invention are preferred (humanized antibodies have been engineered to insert (for example) the mouse complementarity determining regions into a human immunoglobulin framework region, thus reducing the likelihood of an antigenic reaction against the mouse immunoglobulin).

Single or multiple administrations of the compositions can be carried out with dose levels and pattern being selected by the treating physician. In any event, the pharmaceutical formulations should provide a quantity of anti-KS monoclonal antibody of the invention sufficient to effectively treat the patient. Administration should begin at the first indication of undesirable cellular proliferation or shortly after diagnosis, and continue until symptoms are substantially abated and for a period thereafter. In well established cases of disease, loading doses followed by maintenance doses will be required.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the anti-KS monoclonal antibody dissolved or suspended in an acceptable carrier, preferably an aqueous carrier. A variety of aqueous carriers can be used, e.g., water, buffered water, 0.4% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of anti-KS monoclonal antibody of the invention in the pharmaceutical formulations can vary widely, i.e., from less than about 1%, usually at or at least about 10–15% to as much as 50% or more by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 100 mg of anti-KS monoclonal antibody. Actual methods for preparing parenterally administrable compounds will be known or apparent to those skilled in the art and are described in more detail in for example, Remington's Pharmaceutical Science, 17th ed., Mack Publishing Company, Easton, Pa. (1985), which is incorporated herein by reference.

The anti-KS monoclonal antibodies of the invention, or fragments thereof, can also be administered via liposomes. The anti-KS monoclonal antibodies can serve to target the liposomes to Kaposi's sarcoma lesions. Liposomes include emulsions, foams, micelles, insoluble monolayers, liquid crystals, phospholipid dispersions, lamellar layers and the like. In these preparations the monoclonal antibody or fragment to be delivered is incorporated as part of the liposome, alone or in conjunction with a molecule which is, for example, toxic to the target cells. A liposome suspension containing a monoclonal antibody can be administered intravenously, locally, topically, etc. in a dose which varies according to, inter alia, the manner of administration, the peptide being delivered, and the stage of disease being treated.

For solid compositions of the anti-KS monoclonal antibodies of the invention, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more anti-KS monoclonal antibodies, more preferably at a concentration of 25%–75%.

Diagnostic Uses

For diagnostic purposes, the anti-KS monoclonal antibodies, or fragments thereof, can either be labeled or unlabeled. A label is a substance that provides a detectable signal by any of a variety of techniques well known and reported in the art. The monoclonal antibodies of the invention themselves can be directly labeled. Alternatively, unlabeled antibodies included in the invention can be used in combination with other antibodies (second antibodies) that are labelled and that recognize the anti-KS monoclonal antibodies of the present invention. For example, labelled antibodies specific for the constant regions of the anti-KS monoclonal antibodies can be used to detect the monoclonal antibody bound to a sample.

A wide variety of labels can be employed, such as radionuclides, enzymes, enzyme substrates, enzyme cofactors, enzyme inhibitors, ligands (particularly haptens), fluorescers, chemiluminescers, magnetic particles. See, for examples of patents teaching the use of such labels, U.S. Pat. Nos. 3,817,837; 3,850,752; 3,939,350; 3,996,345; 4,277,437; 4,275,149; and 4,366,241, all of which are incorporated by reference.

The anti-KS monoclonal antibodies of the present invention, and fragments thereof, can be used in various immunoassays for detecting Kaposi's sarcoma cells in physiological specimens. Such immunoassay methods can include liquid phase immunoassays and Western blot analysis, competitive and noncompetitive protein binding assays, enzyme-linked immunosorbant assays (ELISA), radioimmunoassays (RIA), and others commonly used and widely described in scientific and patent literature, and many employed commercially. The antibodies of the invention can likewise be employed in immunohistochemical staining techniques by methods well known in the art (see, e.g. Mithen, F. A. (1983) Brain Research 262: 63–69.

The following examples are offered by way of illustration and not limitation.

EXAMPLE 1

Characterization of a Malignant KS Cell Line

A malignant Kaposi's sarcoma cell line, KS Y-1, was derived from a pleural effusion of a Kaposi's sarcoma patient as described herein. KS Y-1 cells have been grown for greater than 92 passages and are thus properly designated a cell line.

Figures 1C, 1D:
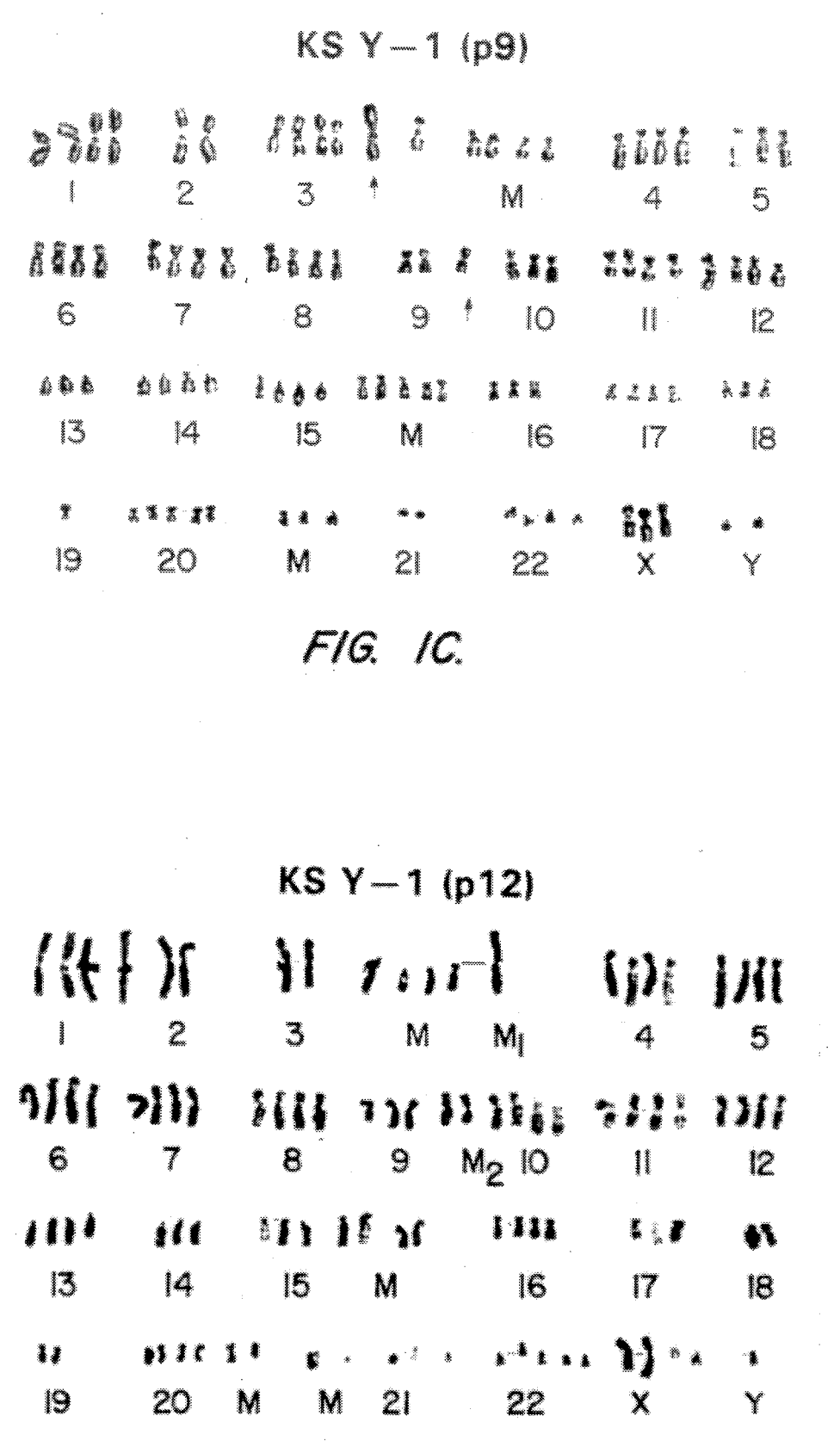

Cells of the KS Y-1 cell line were characterized and their phenotype compared to cells from the previously reported KS cell strains KS-1 and KS-3 (Salahuddin et al., supra.), and with normal endothelial and smooth muscle cells. KS Y-1 cells have a polygonal morphology that changes to a spindle-like phenotype when treated with HTLV-II-infected T cell conditioned medium (CM) (see FIGS. 1A and 1B). The KS Y-1 cells also assume a spindle-like morphology in the absence of CM when the cells reach confluence.

A karyotype analysis of KS Y-1 cells revealed numerous chromosomal aberrations when examined uncultured or at passages 9, 12 (see FIGS. 1C and 1D), 40, and 70. The KS Y-1 cells have a chromosome number in the tetraploid range when examined at metaphase, whether cultured in the presence or absence of HTLV-II-infected T cell conditioned medium. Multiple marker chromosomes and translocated dicentric chromosomes were also detected (see FIGS. 2A and 2B). Similar chromosomal abnormalities were noticed in fresh, KS-enriched cells after being cultured for three days in the absence of HTLV-II CM, demonstrating that the karyotypic abnormalities reflect the situation in vivo and are not a result of long-term culture. These findings for KS Y-1 cells are compatible with previously reported studies that show tetraploidy and chromosomal abnormalities in primary Kaposi's sarcoma lesions and after short-term culture (Bovi et al. (1986) Cancer Res. 46: 6333–6338; Biscaglia, M. (1992) Cancer 69: 793–798; Dictor et al. (1992) Anal. Quant. Cytol. Histol., in press).

Furthermore, KS Y-1 cells can be plated at high efficiency in methylcellulose, a property shared by other tumor cells (Levenbook et al., supra.). In contrast to KS Y-1 cells, previously established KS cell strains (KS-1 to KS-14) do not exhibit cytogenetic abnormalities (Shaw et al., supra.) and do not grow in methylcellulose.

Figure 2B:
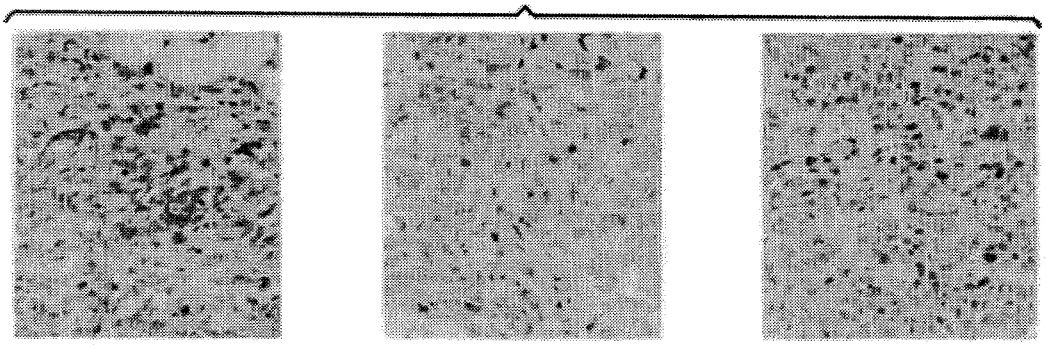
Figure 2B:

The KS Y-1 cells induce angiogenic lesions in nude mice by day 7 (see FIGS. 2A and 2B). HASMC and HUVEC do not induce angiogenesis, while normal bone marrow stromal cells (N-1181 B) cultured in the presence of HTLV-II CM induces a very weak angiogenic response.

The KS Y-1 cell line is able to generate long-lasting tumors (at least one month, and often three months or longer duration) after injection into nude mice and SCID mice (FIG. 2 a,b). $5 \times 10^4$–$5 \times 10^6$ cells were injected into each mouse; mice were sacrificed at 7, 14, and 24 days, and 3 months after injection. Stromal bone marrow cells were injected as controls. Cells obtained from muscle, lung, spleen, and skin tumors in the mice injected with KS Y-1 cells have a human karyotype and similar chromosomal abnormalities as the cultured KS Y-1 cells. In contrast, the short-term angiogenic lesions and transient tumors obtained with the previously described KS cell strains (KS-1 to KS-14) have a mouse karyotype (Salahuddin et al., supra.).

Spindle cells in Kaposi's sarcoma tissues have previously been suggested to be endothelial cells, possibly of lymphatic origin (Salahuddin et al, supra.; Nadji et al. (1981) Arch. Pathol. Lab. Med. 105: 274–275; Beckstead et al., supra.). However, some characteristics typical of endothelial cells are not found on KS Y-1 cells (Table 1). For example, factor VIII-related antigen and antigens for monoclonal antibodies PAL-E and EN-4, which are commonly found in endothelial cells of vascular origin (Holden, C.A., supra.; Jaffe et al., supra.; Burgdor et al., supra.; Cui et al., supra.), are present on human umbilical vein endothelial cells (HUVEC), but not on the KS Y-1 cell line, the KS-3 Kaposi's sarcoma-derived cell strain, or human aortic smooth muscle cells (HASMC).

A ligand for *Ulex europaeus* agglutinin 1 (UEA-1), which specifically recognizes endothelial cells (Orodenez and Batskis, supra.; Beckstead et al., supra.; Russell-Jones et al., supra.; Miettinen et al., supra.), is expressed on KS Y-1 cells, as well as on KS-3 cells, H-UVEC, and HASMC. Similarly, fibronectin and ICAM-1, which are typically expressed by mesenchymal cells (Jaffe et al., supra.) are also expressed by all four of these cell types (Table 1).

KS Y-1 and KS-3 cells both express smooth muscle α actin at high levels, in contrast to H-UVEC. Smooth muscle α actin, considered to be a differentiation marker for smooth muscle cells and pericytes (Skalli et al., *J. Cell. Biol.* 103: 2787–2796) is found in several other non-muscle cell types, especially during various physiologic and pathologic conditions (myofibroblasts during wound healing (Skalli et al. (1989) *Lab. Invest.* 60: 275–285; Darby et al. (1990) *Lab. Invest.* 63: 21–29) and in isolated stroma cells of the bone marrow) (Liosveld et al. (1989) *Blood* 73: 1794–1800).

The markers CD4, CD8, CD10 (fibroblasts, Singer et al. (1984) *Leuk. Res.* 8: 535–545; Brown et al. (1983) *Blood* 61: 718–725), and CD14 (macrophages, Griffier et al. (1981) *J. Clin. Invest.* 68: 932–941; Dimitriu-Bone et al. (1983) *J. Immunol.* 130: 145–152) are absent from the KS Y-1 cell line, as well as from HUVEC, HAMSC, and KS-3 cells (Table 1). All four of these cell lines do express CD25 (IL-2 receptor α chain), p75 (IL-2R β chain), CD71 (transferrin receptor), and the hydrocortisone receptor. The activation of the IL-2 receptor, the transferrin receptor, and the hydrocortisone receptor in the KS Y-1 cell line may contribute to the growth and invasiveness of KS in vivo.

The KS cell lines of the present invention show no evidence of infection with HIV-1, human cytomegalovirus (HCMV), human herpes virus 6 or 7 (HHV-6 or 7), human papilloma virus type 16 (HPV 16), human T-lymphotropic leukemia virus type I or II (HTLV-I or II), herpes simplex virus type 1 or 2, and hepatitis B or C virus. Assays for these viruses included immunofluorescence tests with specific antisera for viral proteins, and polymerase chain reaction (PCR) tests for viral nucleic acids.

EXAMPLE 2

Use of the KS Cell Lines to Test Anti-Kaposi's Sarcoma Agents

The KS cell lines of the present invention can be used to test anticancer reagents by determining the ability of the reagents to inhibit proliferation of the cell lines. For example, the cells are cultured in flat bottomed 96-well tissue culture plates (3072, Falcon Labware) at various cell densities in RPMI1640+FCS medium. Proliferation is evaluated, e.g., via a 4 hour (hr) pulse of $^3$H-thymidine (Amersham, Arlington Heights Ill.) added at 48 hr after culture initiation. Proliferation is said to be "inhibited" by a reagent if cells grown in the presence of the agent incorporate, e.g., about 20% less $^3$H-thymidine than cells grown in the absence of the agent, and preferably about 30% less $^3$H-thymidine than cells not treated with the reagent. Other methods for determining cell proliferation are known in the art and can be employed.

The KS cell lines of the invention are also useful for testing the efficacy of antitumor reagents in vivo. The cell line KS Y-1 was grown for 48 hours in RPMI1640+10% fetal calf serum in the presence of 10–50 μg oncostatin M per ml. Control cells were grown in the absence of oncostatin M. Approximately $5 \times 10^6$ cells were then injected into SCID or nude mice. Neonate, young, adult, male, and female mice were tested.

Mice that were injected with control cells developed large tumors within one week after injection. Mice that had been injected with cells that had been grown in the presence of oncostatin M developed tumors that were about 25 times smaller than the control mice after three months.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A Kaposi's sarcoma cell line, wherein the cell line is KS Y-1 identified as ATCC Accession No. 11448.

2. A method of obtaining a Kaposi's sarcoma cell line, the method comprising:
    a) obtaining malignant Kaposi's sarcoma cells from a metastatic site of a Kaposi's sarcoma patient;
    b) enriching for the malignant Kaposi's sarcoma cells by selectively removing T-lymphocytes, monocytes, macrophages, and fibroblasts by complement-mediated cytotoxicity, using complement in conjunction with antibodies against CD2, CD3, CD4, CD8, CD10, and CD14; and
    c) growing and isolating the enriched Kaposi's sarcoma cells in the absence of exogenously added growth factors.

\* \* \* \* \*